(12) United States Patent
Ochomogo et al.

(10) Patent No.: US 6,454,876 B1
(45) Date of Patent: Sep. 24, 2002

(54) METHOD FOR ELIMINATING MALODORS

(75) Inventors: Maria G. Ochomogo, Danville; Martha J. Adair; Sheila E. Ali, both of San Ramon; Leslie E. Finn; David Peterson, both of Pleasanton; Gregory M. Piché, Dublin; Gregory Van Buskirk, Danville, all of CA (US)

(73) Assignee: The Clorox Company, Oakland, CA (US)

( * ) Notice: Subject to any disclaimer, the term of this patent is extended or adjusted under 35 U.S.C. 154(b) by 0 days.

(21) Appl. No.: 09/469,576

(22) Filed: Dec. 22, 1999

(51) Int. Cl.$^7$ .............. B08B 3/04; C11D 3/37; C11D 3/43

(52) U.S. Cl. .......... 134/42; 510/276; 510/278; 510/279; 510/477; 252/8.91; 424/76.4; 8/137.5

(58) Field of Search ............. 8/137.5, 142; 424/76.4; 252/8.91; 510/276, 278, 279, 477; 134/42

(56) References Cited

U.S. PATENT DOCUMENTS

| | | | |
|---|---|---|---|
| 3,567,118 A | 3/1971 | Sheperd | 239/6 |
| 4,048,369 A | 9/1977 | Johnson | 428/262 |
| 4,184,985 A | 1/1980 | Scheuermann | 252/522 |
| 4,540,721 A | 9/1985 | Staller | 523/102 |
| 4,606,842 A | 8/1986 | Keyes et al. | 252/174.23 |
| 4,934,609 A | 6/1990 | Lindauer et al. | 241/3 |
| 4,938,416 A | 7/1990 | Bertrand et al. | 239/1 |
| 5,094,761 A * | 3/1992 | Trinh et al. | 252/8.9 |
| 5,102,564 A * | 4/1992 | Gardlik et al. | 252/8.9 |
| 5,126,068 A | 6/1992 | Burke et al. | 252/174.21 |
| 5,380,707 A | 1/1995 | Barr et al. | 512/17 |
| 5,578,563 A * | 11/1996 | Trinh et al. | 510/513 |
| 5,593,670 A * | 1/1997 | Trinh et al. | 424/76.1 |
| 5,663,134 A | 9/1997 | Trinh et al. | 510/406 |
| 5,668,097 A * | 9/1997 | Trinh et al. | 510/293 |
| 5,714,137 A * | 2/1998 | Trinh et al. | 424/76.4 |
| 5,783,544 A | 7/1998 | Trinh et al. | 510/293 |
| 5,939,060 A | 8/1999 | Trinh et al. | 424/76.4 |
| 5,942,217 A * | 8/1999 | Woo et al. | 424/76.1 |
| 5,955,093 A * | 9/1999 | Woo et al. | 424/401 |
| 5,955,414 A * | 9/1999 | Brown et al. | 510/279 |
| 5,968,404 A * | 10/1999 | Trinh et al. | 252/8.91 |
| 5,997,759 A * | 12/1999 | Trinh et al. | 252/8.91 |
| 6,001,343 A * | 12/1999 | Trinh et al. | 424/76.4 |
| 6,033,679 A * | 3/2000 | Woo et al. | 424/401 |
| 6,080,387 A * | 6/2000 | Zhou et al. | 424/45 |

FOREIGN PATENT DOCUMENTS

| | | | |
|---|---|---|---|
| GB | 1458836 | 12/1976 | D06M/13/30 |
| GB | 1458837 | 12/1976 | D06M/15/66 |
| GB | 2327882 | 2/1999 | A01N/25/06 |
| WO | WO 96/04938 | 2/1996 | A61L/9/01 |
| WO | WO 97/34986 | 9/1997 | C11D/3/50 |

* cited by examiner

*Primary Examiner*—Lorna M. Douyon
*Assistant Examiner*—Brian P. Mruk
(74) *Attorney, Agent, or Firm*—Joel J. Hayashida

(57) ABSTRACT

The invention provides a method and product for mitigating or eliminating malodor(s) with an aqueous liquid deodorizing composition, in which said composition contains about 0.1–3% water soluble/dispersible polymer, about 0.01–5% fragrance, about 1–20% water soluble/dispersible volatile solvent, and, the remainder, water.

7 Claims, No Drawings

METHOD FOR ELIMINATING MALODORS

BACKGROUND OF THE INVENTION

1. Field of the Invention

The invention relates to a method and product for mitigating or eliminating malodors, particularly those which result from contacting fabrics or other soft surfaces. The method provides for the contacting of the malodor(s) with an aqueous liquid deodorizing composition, the composition containing about 0.1–3% water soluble/dispersible polymer, about 0.01–5% fragrance, 1–25% water soluble/dispersible volatile solvent, with the remainder, water and various aesthetic and functional additives.

2. Brief Statement of the Related Art

Keyes et al., U.S. Pat. No. 4,606,842, discloses a hard surface cleaner containing surfactants, optional fragrance, solvent and polyacrylic acid as a cleaning adjunct. However, Keyes did not teach, disclose, or suggest the use of a water soluble/dispersible polymer in conjunction with a fragrance as an effective malodor counteractant, which results from contacting said malodor and forming at least a partial film thereon. Indeed, Keyes would actually teach away from this concept since it discloses a hard surface cleaner, with which the user would wipe away the dose of cleaner and the stain to leave a substantially barren surface.

Staller, U.S. Pat. No. 4,540,721, discloses a method of fragrancing a container headspace with an aqueous emulsion comprising 4–70% water-emulsifiable or water-soluble polymer, 5–80% scented oil and from about 6–80% water. The aqueous emulsion is cast onto a discrete location in the container and the water volatilizes to leave behind a cast solid impregnated with scented oil. The high solids content of these sorts of emulsions are necessary to effectively deodorize the carton headspace of malodorous oxidants, such as diperoxydodecanedioic acid ("DPDDA"). It is further clear that Staller's emulsion cannot be dosed from a dispenser or other convenient metering device. It is fuirther evident that this type of fragrance metering means is meant not to come in direct contact with the malodor or malodor-causing material, but, instead is located away therefrom.

There are presently some liquid household malodor counteractants, such as aerosols and spray-dispensed liquid compositions. For example, Bertrand et al., U.S. Pat. No. 4,938,416, teaches the combination of 88–99% water, 0.1–5% fragrance oil, 0.1–5% surfactant, along with 0.1–2% preservative. Bertrand advises that it contains virtually no or little isopropyl or ethyl alcohol or other solubilizing alcohols, and opines that this results in formulations which are more ecologically and fire safe. Bertrand's formulations are dosed via a pump sprayer, which atomizes the liquid air freshener. However, neither Bertrand nor other liquid malodor counteractants appear to disclose, teach or suggest that combining a water soluble or dispersible polymer to a fragrance and water formulations would improve the efficacy of the fragrance in mitigating or eliminating malodors which are directly contacted by said formulations.

SUMMARY AND OBJECTS OF THE INVENTION

The invention provides a method and product for eliminating or mitigating malodor(s) by directly contacting the same with an aqueous liquid deodorizing composition, the composition containing about 0.1–3% water soluble/ dispersible polymer, about 0.01–5% fragrance, 1–25% water soluble/dispersible volatile solvent, with the remainder, water. In alternative embodiments, various aesthetic and fimctional additives may be added in low levels, such as surfactants/emulsifiers, fragrances, and preservatives.

It is therefore an object of this invention to provide a method for the counteracting of malodors by contacting them with an aqueous liquid deodorizing composition It is another object of this invention to provide a convenient product for mitigating or eliminating malodors, particularly those deposited on soft surfaces such as fabrics and other absorbent/adsorbent materials.

It is a further object of this invention to provide a trigger sprayer, pump sprayer, aerosol or other consumer-friendly means for delivering the malodor counteractant of this invention.

It is also an object of this invention to provide a long lasting means for malodor control, especially when compared to what is presently commercially available.

It is an additional object of this invention to provide a liquid malodor counteractant which dries rapidly after being sprayed or dosed onto a surface containing a malodor thereon.

DETAILED DESCRIPTION OF THE INVENTION

The invention provides a method and product for eliminating or mitigating malodor(s) by directly contacting the same with an aqueous liquid deodorizing composition, the composition containing about 0.1–3% water soluble/ dispersible polymer, about 0.01–5% fragrance, 1–20% water soluble/dispersible volatile solvent, with the remainder, water. In alternative embodiments, various aesthetic and functional additives may be added in low levels, such as surfactants/emulsifiers, fragrances, and preservatives.

The invention is especially useful for treatment of soft surfaces, such as without limitation, upholstery, draperies, carpets, clothing, rugs, tapestries, porous walls, vehicle compartments (e.g. automobile interiors, cabs, trunks, etc.), pet beds and bedding, clothing hampers and containers (e.g., gym bags and mesh laundry bags), and any other enclosed living, working, leisure and transportation spaces, and the like which are either absorbent or adsorbent, and thus are likely to retain malodors once contacted therewith. These malodors include, without limitation, smoke, food, pet, botanical, animal, other environmental and biological (such as body) malodors.

In the application, effective amounts are generally those amounts listed as the ranges or levels of ingredients in the descriptions which follow here to. Unless otherwise stated, amounts listed in percentage ("%'s") are in weight percent of the composition, unless otherwise noted.

The ingredients constituting the novel liquid malodor eliminating or mitigating composition are described hereinbelow.

1. The Water Soluble/Dispersible Polymer(s)

The polymer is a key component of the invention. It is necessary to provide substantivity via a transparent to slightly visible residue or film which results after application of the inventive liquid composition to a surface.

The polymer is generally speaking a water soluble to dispersible polymer having a molecular weight of generally below 2,000,000 daltons. The polymers will also be not damaging to fabrics, carpets, and other soft surfaces. They should have enough tack or stickiness, when applied and dried, to provide a matrix in which the malodor may be entrapped, but not so much that to the human touch the film or residue feels or imparts an obvious sticky feel. Preferably, the polymer will also not itself have an obvious or offensive odor, although that attribute can be mitigated by judicious selection of fragrance.

Examples of suitable classes of polymers include:

a. Polysaccharides

Suitable polymers may comprise polysaccharide polymers, which include substituted cellulose materials like carboxymethylcellulose, ethyl cellulose, hydroxyethylcellulose, hydroxypropylcellulose, hydroxymethylcellulose, succinoglycan and naturally occurring polysaccharide polymers like xanthan gum, guar gum, locust bean gum, tragacanth gum or derivatives thereof. Particularly useful polysaccharides are xanthan gum and derivatives thereof. Some of these are thickeners which may have too much tack, from a performance and aesthetic standpoint. Additional suitable polysaccharide polymers may include sodium caseinate and gelatin. Other suitable polysaccharide polymers may include cationic derivatives, such as the cationic cellulose ether, Polymer JR.

b. Polycarboxylates

Polycarboxylates can also be used which contain amounts of nonionizable monomers, such as ethylene and other simple olefins, styrene, alpha-methylstyrene, methyl, ethyl and $C_3$ to $C_8$ alkyl acrylates and methacrylates, isobornyl methacrylate, acrylamide, hydroxyethyl acrylate and methacrylate, hydroxypropyl acrylate and methacrylate, N-vinyl pyrrolidone, butadiene, isoprene, vinyl halides such as vinyl chloride and vinylidine chloride, alkyl maleates, alkyl fumarates. Other suitable polymers include other polycarboxylates, such as homopolymers and copolymers of monomeric units selected from the group consisting of unsaturated carboxylic acids such as acrylic acid, methacrylic acid, polycarboxylic acids, sulfonic acids, phosphonic acids and mixtures thereof. Copolymerization of the above monomeric units among them or with other co-monomers such as maleic anhydride, ethylene or propylene are also suitable.

c. Polystyrenesulfonates

Other suitable polymers are polystyrenesulfonates such as Flexan 130 and Versa TL501 from National Starch and Chemical. Polystyrenesulfonates are also useful as copolymers, for example Versa TL-4 also from National Starch and Chemical.

d. Acrylate Polymers

Other suitable polymers are acrylic emulsion polymers used as floor polish coatings. These are generally copolymers of one or more acidic monomers, such as acrylic acid, methacrylic acid or maleic anhydride, with at least one other ethylenically unsaturated monomer selected from a group consisting of ethylene and other simple olefins, styrene, alpha-methylstyrene, methyl, ethyl and $C_3$ to $C_8$ alkyl acrylates and methacrylates, isobornyl methacrylate, acrylamide, hydroxyethyl acrylate and methacrylate, hydroxypropyl acrylate and methacrylate, N-vinyl pyrrolidone, butadiene, isoprene, vinyl halides such as vinyl chloride and vinylidine chloride, alkyl maleates, alkyl fumarates, fumaric acid, maleic acid, itaconic acid, and the like. It is also frequently desirable to include minor amounts of other functional monomers, such as acetoacetoxy methacrylate or other acetoacetate monomers and divinyl or polyvinyl monomers, such as glycol polyacrylates, allyl methacrylate, divinyl benzene and the like. The preferred polymers have an acid number from about 75 to about 500 and a number average molecular weight of about 500 to about 20,000. These polymers may also be crosslinked with metal ions or modified for crosslinking with silane functionality as described, for example, in U.S. Pat. No. 5,428,107. Examples of such acrylic emulsion polymers include those available under the Rhoplex tradename from Rohm & Haas, such as Rhoplex AC-33, Rhoplex B-924, and Rhoplex MC-76. There are also polymers from National Starch and Chemical, such as Amaze, Flexan and Balance CR, Balance 47 and Balance 055. Another preferred polymer is Carboset by B. F. Goodrich. Other suitable polymers are copolymers of acrylic and/or methacrylic acid with acrylate and methacrylate esters. For example, a copolymer of 51% methyl methacrylate, 31% butyl acrylate, and 18% acrylic acid is available from Rohm & Haas as Emulsion Polymer E-1250. Additionally, there are acrylates from Rohm and Haas, namely, Acusol, such as Acusol 445, and the like. See also Keyes et al., U.S. Pat. No. 4,606,842, incorporated herein by reference.

Other suitable polymers may include cationic acrylic water soluble polymers that are copolymers of cationic quatemized acrylates, methacrylates, acrylamides, and methacrylamides, for example trimethylammoniumpropylmethacrylate, and acrylamide or acrylonitrile.

e. Polyethyleneimines

Other suitable polymers are polyethyleneimines and copolymers with other polyalkyleneimines. These amino-functional polymers can also be modified by ethoxylation and propoxylation. These amino-functional polymers can also be quanternized with methyl groups or oxidized to amine oxides.

f. Polyvinylpyrrolidones

Other suitable polymers include vinylpyrrolidone homopolymers and copolymers. Suitable vinylpyrrolidone homopolymers have an average molecular weight of from 1,000 to 100,000,000, preferably from 2,000 to 10,000,000, more preferably from 5,000 to 1,000,000, and most preferably from 30,000 to 700,000. Suitable vinyl pyrrolidone homopolymers are commercially available from ISP Corporation, Wayne, N.J. under the product names PVP K-15 (average molecular weight of 8,000), PVP K30 (average molecular weight of 38,000), PVP K-60 (average molecular weight of 216,000), PVP K-90 (average molecular weight of 630,000), and PVP K-120 (average molecular weight of 2,900,000). Suitable copolymers of vinylpyrrolidone include copolymers of N-vinylpyrrolidone with one or more alkylenically unsaturated monomers. Suitable alkylenically unsaturated monomers include unsaturated dicarboxylic acids such as maleic acid, chloromaleic acid, fumaric acid, itaconic acid, citraconic acid, phenylmaleic acid, aconitic acid, acrylic acid, methacrylic acid, N-vinylimidazole, vinylcaprolactam, butene, hexadecene, and vinyl acetate. Any of the esters and amides of the unsaturated acids may be employed, for example, methyl acrylate, ethylacrylate, acrylamide, methacryamide, dimethylaminoethylmethacrylate, dimethylaminopropylmethacrylamide, trimethylammoniumethylmethacrylate, and trimethylammoniumpropylmethacrylamide. Other suitable alkylenically unsaturated monomers include aromatic monomers such as styrene, sulphonated styrene, alpha-methylstyrene, vinyltoluene, t-butylstyrene and others. Copolymers of vinyl-pyrrolidone with vinyl acetate are commercially available under the trade name PVP/VA from ISP Corporation. Copolymers of vinylpyrrolidone with alpha-olefms are available, for example, as P-904 from ISP Corporation. Copolymers of vinylpyrrolidone with dimethylaminoethylmethacrylate are available, for example, as Copolymer 958 from ISP Corporation. Copolymers of vinylpyrrolidone with trimethylammoniumethylmethacrylate are available, for example, as Gafquat 734 from ISP Corporation. Copolymers of vinylpyrrolidone with trimethylammoniumpropylmethacrylamide are available, for example, as Gafquat HS-100 from ISP Corporation. Copolymers of vinylpyrrolidone with styrene are available, for example, as Polectron 430 from ISP Corporation. Copolymers of vinylpyrrolidone with acrylic acid are available, for example, as Polymer ACP 1005 (25% vinylpyrrolidone/75% acrylic acid) from ISP Corporation.

g. Methylvinyl ether

Other suitable polymers include methylvinylether homopolymers and copolymers. Preferred copolymers are those with maleic anhydride. These copolymers can be hydrolyzed to the diacid or derivatized as the monoalkyl ester. For example, the n-butyl ester is available as Gantrez ES-425 from ISP Corporation.

h. Polyvinyl alcohols

Other suitable polymers include polyvinyl alcohols. Preferably, polyvinyl alcohols which are at least 80.0%, preferably 88–99.9%, and most preferably 99.0–99.8% hydrolyzed are used. For example, the polyvinyl alcohol, Elvanol 71-30 is available from E. I. DuPont de Nemours and Company, Wilmington, Del.

i. Polyethylene glycols

Yet other feasible polymers may be polyethylene glycols, such as disclosed in Baker et al., U.S. Pat. No. 4,690,779, incorporated herein by reference.

Mixtures of any of the foregoing polymers may be possible or desirable. The hydrophilic polymer or polymers are present at a level of about 0.1–3% of the liquid composition.

2. Fragrances

Fragrances, which are usually lipophilic oils, such as, without limitation, materials which can also function as solvents, such as terpenes and their derivatives, Representative examples for each of the above classes of terpenes with finctional groups include but are not limited to the following: Terpene alcohols, including, for example, cis-2-pinanol, pinanol, thymol, 1,8-terpin, dihydro-terpineol, tetrahydro-myrcenol, tetrahydrolinalool, and tetrahydroalloocimenol; and terpene ethers, including, for example, benzyl isoamyl ether, 1,8-cineole, 1,4-cineole, isobomyl methylether, methyl hexylether. Further, other tertiary alcohols are useful herein. Additional useful solvents include alicyclic hydrocarbons, such as methylcyclo-hexane. Terpene hydrocarbons with functional groups which appear suitable for use in the present invention are discussed in substantially greater detail by Simonsen and Ross, The Terpenes, Volumes I-V, Cambridge University Press, 2nd Ed., 1947 (incorporated herein by reference thereto). See also, co-pending and commonly assigned Choy, U.S. Pat. No. 5,279,728, incorporated herein by reference thereto. Other fragrances are found amongst combinations of aldehydes, esters, essential oils, and the like. See, Bertrand et al., U.S. Pat. No. 4,938,416, Swatling et al, U.S. Pat. No. 5,227,366, Schleppnik et al., U.S. Pat. No. 4,009,253, Berger, U.S. Pat. No. 4,137,251, and Schleppnik, U.S. Pat. Nos. 4,310,512 and 4,622,221, all of which are incorporated herein by reference. Fragrances are available from such vendors as Givaudan-Rohre, International Flavors and Fragrances, Firmenich, Norda, Bush Boake and Allen, Quest and others. The amount of fragrance necessary for effective malodor counteractancy should be in the range of from about 0.01–5%, more preferably about 0.01–3%, of the liquid composition.

3. The Organic Solvent(s)

The solvents useful in this invention are organic solvents with a vapor pressure of at least 0.001 mm Hg at 25° C. and soluble to the extent of at least 1g/100 ml water. The upper limit of vapor pressure appears to be about 100 mm Hg at 25° C. Vapor pressure is a useful measure for determining the applicability of the given solvent, since one would select a solvent which will volatilize sufficiently so as to leave no visible residue. The organic solvent of the invention is preferably selected from $C_{1-6}$ alkanol, $C_{1-24}$ alkylene glycol ether, and mixtures thereof. The $C_{1-6}$ alkanol solvents are preferred for use. The alkanol can be selected from methanol, ethanol, n-propanol, isopropanol, butanol, pentanol, hexanol, their various positional isomers, and mixtures of the foregoing. In the invention, it has been found most preferable to use ethanol, which has particularly good volatilization and solubilization characteristics. It may also be possible to utilize in addition to, or in place of, said alkanols, the diols such as methylene, ethylene, propylene and butylene glycols, and mixtures thereof. Other solvents, such as amines, ketones, ethers, hydrocarbons and halides may be useful. Other examples of solvents can be found in Kirk-Othmer, Encyclopedia of Chemical Technology 3rd, Vol. 21, pp. 377–401 (1983), incorporated by reference herein.

The alkylene glycol ether solvents can include ethylene glycol monobutyl ether, ethylene glycol monopropyl ether, propylene glycol monopropyl ether, propylene glycol monobutyl ether, and mixtures thereof.

It is preferred to limit the total amount of solvent to no more than 25%, more preferably no more than 15%, and most preferably, no more than 10%, of the composition. However, a particularly preferred level of solvent is about 9%, for optimal drying of the liquid to result in the desired film. Moreover, in some of the compositions of this invention, no solvent may be present. A preferred range is about 1–15%.

On the other hand, in some of the embodiments of the invention, an aerosol delivery is preferred. In such case, a propellant, such as a hydrocarbon blend (e.g., propane/isobutene), dimethyl ether, or other compressible gases, or, in the case of non-compressible gases, carbon dioxide, is included. When counted against the solvent level, the propellant will actually raise the solvent level to a minimum of about at least 15%, more preferably at least 25%, of the composition. The water level would be decreased correspondingly.

4. Water

The fourth principal ingredient is water, which should be present at a level of at least about 75%, more preferably at least about 80%, and most preferably, at least about 85%. Deionized water is most preferred. Water forms the predominant, continuous phase in which the ingredients are solubilized or dispersed.

In those applications where an aerosol form is desired and water forms the predominant, continuous phase, the water should be present at a level of at least about 55% to allow for use of propellant. However, the formula delivered to the surface after volatilization of the propellant will be essentially that described above, including water present at a level of at least 75%, more preferably at least about 80%, and most preferably, at least about 85%.

5. Aesthetic/Functional Additives

Various Desirable Actives include:

a. Surfactants

The surfactants used in the invention may be one or more nonionic surfactants which have a HLB of about 3–16. For a further discussion of HLB measurements, one should consult Popiel, *Introduction to Colloid Science* (1978), pp. 43–44 and Gerhartz, *Ullmann's Encyclopedia of Industrial Chemistry*, 5th Ed., Vol. A9 (1985), pp. 322–23, both of which are incorporated by reference thereto.

Surfactants may be selected from linear and branched alkoxylated alcohols, alkoxylated alkylphenols and alkylpolyglycosides, among others. The alkoxylated alcohols include ethoxylated, propoxylated, and ethoxylated and propoxylated $C_{5-20}$ alcohols, with about 1–5 moles of ethylene oxide, or about 1–5 moles of propylene oxide, or 1–5 and 1–5 moles of ethylene oxide and propylene oxide, respectively, per mole of alcohol. There are a wide variety of products from numerous manufacturers, such as the Neodol series from Texaco Chemical Co., to wit, Neodol 25-3, a linear $C_{12-15}$ alcohol ethoxylate with 3 moles of ethylene oxide ("EO") per mole of alcohol, HLB of 7.8, and Neodol 91-2.5, a linear $C_{9-11}$ alcohol ethoxylate with 2.5 moles of EO; Alfonic 1412-40, a $C_{12-14}$ ethoxylated alcohol with 3 moles of EO from Conoco; Surfonic L12-2.6, a C10-12 ethoxylated alcohol with 3 moles of EO, and Surfonic L24-3, a $C_{12-14}$ ethoxylated alcohol with 3 moles of EO from Huntsman Chemical; and Tergitol 25-L-3, a $C_{12-15}$ ethoxylated alcohol with 3 moles of EO, from Union Carbide. The secondary ethoxylated alcohols include Tergitol 15-S-3, a $C_{11-15}$ secondary ethoxylated alcohol, with 3 moles of EO, from Union Carbide.

The branched surfactants, especially preferred of which are tridecyl ethers, include Trycol TDA-3, a tridecyl ether with 3 moles of EO, from Henkel KGaA (formerly, Emery), and Macol TD 3, a tridecyl ether with 3 moles of EO, from PPG Industries. See, also, *McCutcheon's Emulsifiers and Detergents*, 1987. The sparingly soluble nonionic surfactant can also be selected from alkoxylated alkylphenols, such as: Macol NP-4, an ethoxylated nonylphenol with 4 moles of EO, and an HLB of 8.8, from PPG; Triton N-57, an ethoxylated nonylphenol with an HLB of 10.0, Triton N-42, an ethoxylated nonylphenol with an HLB of 9.1, both from Rohm & Haas Co.; and Igepal CO-520, with an HLB of 10.0, an ethoxylated nonylphenol from GAF Chemicals Corp.; Alkasurf NP-5, with an HLB of 10.0, and Alkasurf NP-4, with an HLB of 9.0, both of which are ethoxylated nonylphenols from Alkaril Chemicals; Surfonic N-40, with an HLB of 8.9, an ethoxylated nonylphenol from Huntsman. See, *McCutcheon's Emulsifiers and Detergents* (1987), especially page 282, incorporated herein by reference thereto. The nonionic surfactant can be chosen from, among others: Alfonic surfactants, sold by Conoco, such as Alfonic 1412–60, a $C_{12-14}$ ethoxylated alcohol with 7 moles of EO; Neodol surfactants, sold by Shell Chemical Company, such as Neodol 25-7, a $C_{12-15}$ ethoxylated alcohol with 7 moles of EO, Neodol 45-7, a $C_{14-15}$ ethoxylated alcohol with 7 moles of EO, Neodol 23-5, a linear $C_{12-13}$ alcohol ethoxylate with 5 moles of EO, HLB of 10.7; Surfonic surfactants, also sold by Huntsman Chemical Company, such as Surfonic L12-6, a $C_{10-12}$ ethoxylated alcohol with 6 moles of EO and L24-7, a $C_{12-14}$ ethoxylated alcohol with 7 moles of EO; and Tergitol surfactants, both sold by Union Carbide, such as Tergitol 25-L-7, a C12-15 ethoxylated alcohol with 7 moles of EO, and Tergitol S-15-7, a $C_{11-15}$ ethoxylated alcohol with 7 moles of EO. Macol NP-6, an ethoxylated nonylphenol with 6 moles of EO, and an HLB of 10.8, Macol NP-9.5, an ethoxylated nonylphenol with about 11 moles EO and an HLB of 14.2, Macol NP-9.5, an ethoxylated nonylphenol with about 9.5 moles EO and an HLB of 13.0, both from Mazer Chemicals, Inc.; Triton N-101, an ethoxylated nonylphenol with 9–10 moles of ethylene oxide per mole of alcohol ("EO") having a hydrophile-lipophile balance ("HLB") of 13.4, Triton N-111, an ethoxylated nonylphenol with an HLB of 13.8, both from Rohm & Haas Co.; Igepal CO-530, with an HLB of 10.8, Igepal CO-730, with an HLB of 15.0, Igepal CO-720, with an HLB of 14.2, Igepal CO-710, with an HLB of 13.6, Igepal CO-660, with an HLB of 13.2, Igepal CO-620, with an HLB of 12.6, and Igepal CO-610 with an HLB of 12.2, all polyethoxylated nonylphenols from GAF Chemicals Corp.; Alkasurf NP-6, with an HLB of 11.0, Alkasurf NP-15, with an HLB of 15, Alkasurf NP-12, with an HLB of 13.9, Alkasurf NP-I1, with an HLB of 13.8, Alkasurf NP-10, with an HLB of 13.5, Alkasurf NP-9, with an HLB of 13.4, and Alkasurf NP-8, with an HLB of 12.0, all polyethoxylated nonylphenols from Alkaril Chemicals; and Surfonic N-60, with an HLB of 10.9, and Surfonic N-120, with an HLB of 14.1, Surfonic N-102, with an HLB of 13.5, Surfonic N-100, with an HLB of 13.3, Surfonic N-95, with an HLB of 12.9, and Surfonic N-85, with an HLB of 12.4, all polyethoxylated nonylphenols from Huntsman.

The glycosides, particularly the alkyl polyglycosides, may also be used as a surfactant for purposes of the aerosol formulation of the present invention. These glycosides include those of the formula:

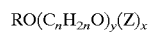

$$RO(C_nH_{2n}O)_y(Z)_x$$

wherein R is a hydrophobic group (e.g., alkyl, aryl, alkylaryl etc., including branched or unbranched, saturated and unsaturated, and hydroxylated or alkoxylated members of the foregoing, among other possibilities) containing from about 6 to about 30 carbon atoms, preferably from about 8 to about 15 carbon atoms, and more preferably from about 9 to about 13 carbon atoms; n is a number from 2 to about 4, preferably 2 (thereby giving corresponding units such as ethylene, propylene and butylene oxide); y is a number having an average value of from 0 to about 12, preferably 0; Z is a moiety derived from a reducing saccharide containing 5 or 6 carbon atoms (e.g., a glucose, fructose, mannose, galactose, talose, gulose, allose, altrose, idose, arabinose, xylose, lyxose, or ribose unit, etc., but most preferably a glucose unit); and x is a number having an average value of from 1 to about 10, preferably from 1 to about 5, and more preferably from 1 to about 3. It would be apparent that a number of variations with respect to the makeup of the glycosides are possible. For example, mixtures of saccharide moieties (Z) may be incorporated into polyglycosides. Also, the hydrophobic group (R) can be attached at the 2-, 3-, or 4-positions of a saccharide moiety rather than at the 1-position (thus giving, for example, a glucosyl as opposed to a glucoside). In addition, normally free hydroxyl groups of the saccharide moiety may be alkoxylated or polyalkoxylated. Further, the $(C_nH_{2n}O)_y$ group may include ethylene oxide and propylene oxide in random or block combinations, among a number of other possible variations.

An exemplary glycoside surfactant is APG 325n, which is manufactured by the Henkel Corporation. APG 325n is a nonionic alkyl polyglycoside in which R is a mixture of $C_9C_{10}$ and $C_{11}$ chains in a weight ratio respectively of 20:40:40 (equivalent to an average of $C_{10.2}$), with x of 1.6, and an HLB of 13.1.

The amine oxides, referred to as mono-long chain, di-short chain, trialkyl amine oxides, have the general configuration:

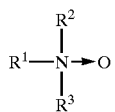

wherein $R^1$ is $C_{6-24}$ alkyl, and $R^2$ and $R^3$ are both $C_{1-4}$ alkyl, or $C_{1-4}$ hydroxyalkyl, although $R^2$ and $R^3$ do not have to be equal. These amine oxides can also be ethoxylated or propoxylated. The preferred amine oxide is lauryl amine oxide. The commercial sources for such amine oxides are Barlox 10, 12, 14 and 16 from Lonza Chemical Company, Varox by Witco and Ammonyx by Stepan Company.

A further semi-polar nonionic surfactant is alkylamidoalkylenedialkyl-amine oxide. Its structure is shown below:

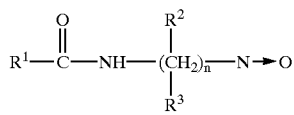

wherein $R^1$ is $C_{5-20}$ alkyl, $R^2$ and $R^3$ are $C_{1-4}$ alkyl,

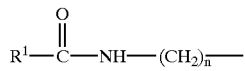

or —$(CH_2)_p$—OH, although $R^2$ and $R^3$ do not have to be equal or the same substituent, and n is 1–5, preferably 3, and p is 1–6, preferably 2–3. Additionally, the surfactant could be ethoxylated (1–10 moles of EO/mole) or propoxylated (1–10 moles of PO/mole). This surfactant is available from various sources as a cocoamidopropyldimethyl amine oxide; it is sold by Lonza Chemical Company under the brand name Barlox C. Additional semi-polar surfactants may include phosphine oxides and sulfoxides.

In some applications, such as when an aerosol version of the formulation is contemplated, there may be a need to add a defoamer, or to judiciously select a surfactant, or blend of surfactants, which will eliminate or mitigate any undesirable foaming.

It is possible that other surfactants may be suitable for use herein: anionic surfactants, such as, without limitation, alkali metal alkyl sulfates, alkylarylsulfonates, primary and secondary alkane sulfonates (also referred to as paraffin sulfonates), alkyl diphenyloxide disulfonates, and mixtures thereof; cationic surfactants, such as, without limitation, quaternary ammonium, imidazolinium, morpholinium, and other such surfactants; amphoteric surfactants, such as, without limitation, an alkylbetaine, an amidobetaine (especially alkylpropylamidodialkylbetaines, eg., Velvetex AB, from Henkel KGaA), or a sulfobetainedialkylbetaines; and zwitterionic surfactants can be found described in Jones, U.S. Pat. No. 4,005,029, at columns 11–15, which are incorporated herein by reference.

The amount of the surfactants is generally between about 0.01 to about 5%, more preferably between about 0.01 to about 3%, and most preferably between about 0.01 to 1%, of the aqueous composition. Higher levels of surfactants are not preferred in the composition due to the tendency of the surface to which the surfactant is contacted becoming more tacky, and thus more prone to re-soiling.

c. Dyes and Colorants

Dyes and colorants which can be solubilized or suspended in the formulation. A wide variety of dyes or colorants can be used to impart an aesthetically and commercially pleasing appearance. The amounts of these aesthetic adjuncts should be in the range of 0–2%, more preferably 0–1%.

d. Antimicrobials

Additionally, because the surfactants in liquid systems are sometimes subject to attack from microorganisms, it is advantageous to add a preservative, i.e., mildewstat or bacteristat. Exemplary mildewstats (including non-isothiazolone compounds) include Kathon GC, a 5-chloro-2-methyl-4-isothiazolin-3-one, Kathon ICP, a 2-methyl-4-isothiazolin-3-one, and a blend thereof, and Kathon 886, a 5-chloro-2-methyl-4-isothiazolin-3-one, all available from Rohm and Haas Company; Bronopol, a 2-bromo-2-nitropropane 1,3-diol, from Boots Company Ltd.; Proxel CRL, a propyl-p-hydroxybenzoate, from ICI PLC; Nipasol M, an o-phenyl-phenol, $Na^+$ salt, from Nipa Laboratories Ltd.; Integra 44 (a sodium hydroxymethylglycinate) from ISP; Dowicide A, a 1,2-benzoisothiazolin-3-one, from Dow Chemical Co.; and Irgasan DP 200, a 2,4,4'-trichloro-2-hydroxydiphenylether, from Ciba-Geigy A. G. See also, Lewis et al., U.S. Pat. No. 4,252,694 and U.S. Pat. No. 4,105,431, incorporated herein by reference. Other actives include, without limitation, quaternary ammonium compounds, "polyquats," which are reaction products/mixtures of anionic polymer or prepolymers with quaternary ammonium compounds, phenols, 3-isothiazolones, methyl and propyl parabens, and the like. These antimicrobial materials may be desirable to be delivered to a particular surface, such as fabrics, or hard surfaces, so as to deliver residual antimicrobial activity. Especially preferred are the polyquats which are referred to in Zhou, U.S. patent application Ser. No. 08/833,276, filed Apr. 4, 1997, now U.S. Pat. No. 6,017,561 and Zhou et al., U.S. patent application Ser. No. 09/116,190, filed Jul. 15, 1998, now U.S. Pat. No. 6,080,387 both of common assignment, and incorporated herein by reference thereto.

e. Miscellaneous Adjuncts

Small amounts of adjuncts can be added for improving aesthetic qualities of the invention. Other desirable additives may include chelating agents (without limitation, such as alkali metal salts of EDTA, preferably tetrapotassium EDTA; See Robbins et al., U.S. Pat. No. 5,972,876, incorporated herein by reference; or tetraammonium EDTA; see Mills et al., U.S. Pat. No. 5,814,591, incorporated herein by reference) salts, pigments, colorants and the like. Additional surfactants (anionic, nonionic, cationic, amphoteric, zwitterionic and mixtures), hydrotropes, solvents, and other dispersing aids may also be added in discrete amounts, taking into account their individual performance attributes and whether their addition may affect the product stability. For example, an especially preferred wetting agent/dispersing aid is a polyether modified polydimethylsiloxane known as BYK. Buffering agents, such as borax, or, more accurately, di-alkali metal tetraborate n-hydrate (preferably, $Na_2B_4O_7$ x $nH_2O$, where n=0–10, most preferably, 4, 5 or 10), may be used in the invention. The alkali metal counterion may be selected from sodium, potassium or lithium, or a combination thereof. Borax decahydrate is the most commonly found form of borax and is the compound assumed when one discusses borax. Borax pentahydrate is another preferred compound. Other boron-based compounds potentially suitable for use are disclosed in *Kirk-Othmer, Encyclopedia of Chemical Technology*, 3rd Ed., Vol. 4, pp. 67–109 (1978), said pages being incorporated herein by reference. Borax can be obtained from such vendors as U.S. Borax and North American Borax.

In the following Experimental section, examples of the inventive composition are provided.

EXPERIMENTAL

In the following section, examples of various embodiments of the invention are depicted. Where ingredients are repeated in some of the Examples, and have been previously identified in footnotes in prior Examples, those footnotes are not repeated.

Example 1

Aqueous Liquid Malodor Eliminating/Mitigating Composition

| Ingredient | Weight % |
| --- | --- |
| Deionized Water[1] | 90.70 (q.s. to 100%) |
| Acrylic Polymer Emulsion[2] | 1.08 |
| Ethanol[3] | 5.00 |
| Polyether modified Polydimethylsiloxane[4] | 0.03 |
| Perservative[5] | 0.10 |
| Nonionic Surfactant[6] | 0.50 |
| Fragrance[7] | 0.20 |
| Potassium Borax[8] | 0.70 |
| Total: | 100.00% |

[1]May not necessarily need to be deionized
[2]Carboset polymer, BF Goodrich
[3]Solvent, MidWest Grain
[4]BYK Chemie
[5]Integra
[6]Union Carbide.
[7]Bush Boake and Allen.
[8]U.S. Borax These ingredients are merely admixed together, with gentle stirring. The preferred order of addition is to disperse the fragrance via the surfactant and to neutralize the polymer (although one can purchase versions that are already neutralized). So, to disperse the fragrance adequately, a preblend of water, surfactant and fragrance, and then this preblend is added to the bulk of the product. The finished liquid malodor mitigating composition can then be loaded into trigger or pump sprayers. Preferably, but by no means limiting to the invention, the composition is delivered in a trigger sprayer made of high density polyethylene (HDPE) or polypropylene, although it is desirable to use transparent polyvinyl chloride (PVC) or, especially, polyethylene terphthalate (PET), and other transparent or translucent thermopolymers. Examples of such sprayers are depicted in Hefter et al., U.S. Des Pat. No. 404,650, Bolliger et al., U.S. Des Pat. No. 401,504, and Malmquist, U.S. Des Pat. No. 372,428, all of which are incorporated herein by reference.

In application, a fine spray or mist is applied to a surface having the malodor(s) thereon. It has been determined that after the malodor(s) have been wetted, and then allowed to dry, the malodor(s) are thus entrapped in the minute, transparent residue or film This has been observed to be especially effective at malodor mitigation or elimination. Because the quantity of product used is very sparing, the invention presents an extremely cost-effective solution to the elimination or mitigation of these particular malodors in enclosed living, working and gathering spaces.

In Example 2, various alternative polymers were screened.

Example 2

| Ingredient | Wt. % |
| --- | --- |
| D.I. Water | q.s. |
| Polymer[1] | 1.08 |
| Ethanol | 5.00 |
| Wetting Agent[2] | 0.03 |
| Fragrance | 0.20 |
| Nonionic Surfactant[3] | 0.50 |
| Potassium Borax | 0.70 |
| Total | 100.00 |

[1]See Table I below
[2]BYK Chemie (polyether modified polydimethylsiloxane)
[3]Tergitol To the above base formulation, a number of different water soluble or dispersible polymers were tested. While all were acceptable, some were preferred due to aesthetic criteria.

TABLE I

| Polymer | Manufacturer | Odor | Film | Performance versus Smoke Malodor |
| --- | --- | --- | --- | --- |
| Carboset | B.F Goodrich | Good | Sticky | Good |
| Amphomer HC | Nat'l Starch & Chem. | Good | Sticky | Good |
| Balance 47 | Nat'l Starch & Chem. | Not Good | Sticky | Good |
| Amaze | Nat'l Starch & Chem. | Good | Smooth | Good |
| Balance CR | Nat'l Starch & Chem. | Good | Sticky | Not Good* |
| Flexam 130 | Nat'l Starch & Chem. | Not Good | Smooth | Good |
| Balance O/55 | Nat'l Starch & Chem. | Good | Smooth | Good |

*Possibly anomalous result

In the next set of examples, drying time differences between the higher solvent level formulas (9%) demonstrated that such higher solvent levels are preferred for product performance.

Examples 3–5

Cotton/polyester and Cotton/acrylic blend swatches were dosed with 0.6 to 0.9 g of two different formulas, one having the constituents depicted in Example 1, above, the second, having 9% ethanol. Each wetted swatch was promptly weighed to get an initial weight, and then weighed again at 12, 18 and 24 minute intervals. Samples were randomized. The difference between drying times for the two different formulas were averaged, the standard deviations and the 95% confidence intervals were then determined.

TABLE 2

Drying Time Improvements

TABLE 2

| | Drying Time Improvements | | |
| --- | --- | --- | --- |
| Example | 3 | 4 | 5 |
| Time | 12 Minutes | 18 Minutes | 24 Minutes |
| Differences | 4.0% | 5.2% | 6.1% |

TABLE 2-continued

Drying Time Improvements

| Example | 3 | 4 | 5 |
|---|---|---|---|
| Is Mean significantly different from 0? | Yes | Yes | Yes |

The next set of examples depict aerosol formulations. However, cost, the presence of an additional solvent (the propellant) and the ensuing reduction in water content, are considerations in aerosol delivery. If aerosol delivery is practiced, there are also preferred systems described in co-pending patent application Ser. No. 09/116,190, of Boli Zhou et al, filed Jul. 15, 1998, now U.S. Pat. No. 6,080,387 and incorporated herein by reference.

Examples 6–9

Aerosol Formulations

Example 6

| Ingredient | Wt. % | Name |
|---|---|---|
| Propellant | 15% | Propane/Isobutane Blend |
| Polymer | 2.00% | Carboset |
| Solvent* | 25% | Ethanol |
| Corrosion Inhibitors | 2.5% | Various |
| Water | q.s. | |

*Higher solvent level necessary to mitigate foaming.

Example 7

| Ingredient | Wt. % | Name |
|---|---|---|
| Propellant | 20% | Propane/Isobutane Blend |
| Polymer | 2.00% | Balance |
| Solvent | 10% | Ethanol |
| Corrosion Inhibitors | 1.9% | Various |
| Water | q.s. | |

Example 8

| Ingredient | Wt. % | Name |
|---|---|---|
| Propellant | 27.5% | Dimethylether |
| Polymer | 2.00% | Carboset |
| Solvent | 8.0% | Ethanol |
| Nonionic Surfactant | 0.50% | Tergitol |
| Corrosion Inhibitors | 1.9% | Various |
| Water | q.s. | |

Example 9 was a variation of Example 8, in which 0.30% of a single corrosion inhabitor was used. In the examples, appropriate metal cans and valves were used. In Example 6 and 7, lined cans were used, while Examples 8 and 9 used unlined cans. These cams are stabd for over a period of months. The formulation of each can was neutralized to pH of ~8–10.

In the following examples, the inventive formulation was compared for performance aganist smoke, which is one of the most common and problematic of household malodoros. It was tested against a competitive refresher product and under different conditions.

Examples 10–14

In this test, fabric samples were tested for smoke odor. A control (no smoke) and a smoke treated swatch represented the extremes of testing. The samples were graded in a blind test by a panel of expert graders, who graded on a 1 (no smoke odor) to 6 (extremely strong smoke oder) scale. Here are the results:

| Example | Product Tested | Score |
|---|---|---|
| 10 | No Smoke | 1.38 |
| 11 | Formula of Eg. 1[1] | 2.41 |
| 12 | Formula of Eg. 1[2] | 2.66 |
| 13 | Commercial Refresher | 2.83 |
| 14 | Smoke only | 4.69 |

[1]Freshly made
[2]Aged (simulated)

The examples 11–13 demonstrate that each was effective against smoke odor, and that the invention performs well even after aging. The invention numerically outperformed the commercial refresher, although because of the numerical bunching, the scoring is not within the 95% confidence level for difference.

Additionally, in another test, formulas made with and without polymer and tested for efficacy against smoke odor on fabric swatches. These samples were then ranked by an odor and fragrance expert for intensity of smoke malodor. The ranking showed that the addition of polymer improved efficacy on smoke malodor.

In a final set of tests, the inventive malodor counteractant was tested for efficacy in eliminating smoke malodor versus water alone, and versus no treatment. Swatches were exposed to cigarette smoke for 10 minutes (with one swatch reserved and not exposed to set one standard), then treated with either 4 sprays of product, 4 sprays of water, or with no treatment with a "counteractant," and allowed to dry overnight. An expert panel then evaluated the swatches and graded on a 1 to 6 scale (with 1 being best, and 6 being worse). The scores are set forth below in Examples 15–18:

| Example | Product Tested | Score |
|---|---|---|
| 15 | No Smoke, No Treatment | 1.6 |
| 16 | Formula of Eg. 1 and Smoke | 2.3 |
| 17 | Water and Smoke | 4.3 |
| 18 | Smoke only | 4.8 |

The invention is further defined by the claims which follow hereto:

What is claimed is:

1. A method for the elimination or mitigation of malodor (s) on surfaces comprising contacting said malodor(s) with an aqueous liquid deodorizing composition, in which said composition comprises about 0.1–3% water soluble/dispersible film-forming polymer, about 0.01–5% fragrance, about 1–15% water soluble/dispersible volatile solvent, about 0.01–1% of a surfactant, and, the remainder, water.

2. The method of claim 1 wherein said composition further comprises at least one aesthetic or functional additive other than said perfume and said surfactant, or mixtures thereof.

3. The method of claim 1 wherein said polymer is selected from the group consisting of water soluble to dispersible polymers having a molecular weight of below about 2,000,000 daltons.

4. The method of claim 3 wherein said polymer is an acrylate polymer.

5. The method of claim 1 wherein said solvent is selected from $C_{1-6}$ alkanols and $C_{1-24}$ glycol ethers.

6. The method of claim 1 wherein said surfaces are soft surfaces.

7. The method of claim 1 wherein said composition additionally comprises at least one propellant.

* * * * *